United States Patent [19] [11] 4,447,669
Hamon et al. [45] May 8, 1984

[54] PRODUCTION OF HYDROCARBONS FROM METHANOL IN THE PRESENCE OF ZEOLITE CATALYSTS

[75] Inventors: Christian Hamon, Saint Nazaire; Jean Bandiera, Lyons; Michel Senes, La Baule, all of France

[73] Assignee: Societe Chimique de la Grande Paroisse, Azote et Produits Chimiques, Paris, France

[21] Appl. No.: 450,910

[22] Filed: Dec. 17, 1982

[30] Foreign Application Priority Data

Jan. 4, 1982 [FR] France ........................... 82 00011

[51] Int. Cl.$^3$ .................... C07C 1/20; C07C 1/00
[52] U.S. Cl. ............................ 585/640; 585/324; 585/408; 585/469; 585/639; 585/733; 502/78
[58] Field of Search ............... 585/315, 322, 324, 408, 585/469, 640, 639, 739; 252/455 Z

[56] References Cited

U.S. PATENT DOCUMENTS

| | | | |
|---|---|---|---|
| 3,551,353 | 10/1968 | Chen et al. | 502/78 |
| 3,728,408 | 4/1973 | Tobias | 585/640 |
| 4,052,472 | 10/1977 | Givens et al. | 585/640 |
| 4,273,753 | 6/1981 | Chang | 502/71 |

FOREIGN PATENT DOCUMENTS

| | | | |
|---|---|---|---|
| 2019913 | 6/1970 | France | 585/640 |
| 1379257 | 2/1975 | United Kingdom | 585/640 |

OTHER PUBLICATIONS

Jong et al., C. R. Hebd Seances Acad. Sci. Ser. C., 1979, 288(8), 245–248, (CA 91:125833j).

Primary Examiner—Delbert E. Gantz
Assistant Examiner—A. Pal
Attorney, Agent, or Firm—Browdy & Neimark

[57] ABSTRACT

Production of unsaturated hydrocarbons of 2–5 carbon atoms from methanol in the presence of zeolitic catalysts is effected by introducing gaseous methanol into a carrier gas, the concentration of the methanol in the entering mixture being between 5 and 60% by volume, and passing the mixture through a catalytic bed based on synthetic mordenite of the so-called de-aluminized type whose Si/Al ratio (atomic) is higher than 80, the flow rate of the methanol being between 1 and 5 liters of liquid methanol per liter of catalyst and per hour. The reaction is carried out at a temperature between 350° and 550° C., under a pressure which can reach 20 bars. The de-aluminized synthetic mordenite is prepared by subjecting the mordenite to a series of alternate acid and hydrothermic treatments, the said series commencing with an acid treatment and terminating with an acid treatment.

15 Claims, No Drawings

PRODUCTION OF HYDROCARBONS FROM METHANOL IN THE PRESENCE OF ZEOLITE CATALYSTS

FIELD OF THE INVENTION

The present invention made with the cooperation of the Catalysis Research Institute, relates to the production of hydrocarbons from methanol in the presence of zeolite catalysts of the mordenite type, and more particularly the production of unsaturated hydrocarbons having from 2 to 5 carbon atoms, called light olefinic hydrocarbons.

BACKGROUND OF THE INVENTION

Methanol is available from carbon-containing sources of non-petroleum origin, such as coal for the synthetic gas route and vegetable matter by cellulose conversion. Thus, this alcohol is bound to become an essential chemical basic material for the manufacture of important synthetic intermediates. The production of light olefinic hydrocarbons from methanol is hence an attractive direction of research.

The reaction of the conversion of methanol into hydrocarbons has been the subject of numerous studies. The catalysts applied belong mostly to the class of zeolites. These crystalline silicoaluminates are particularly suitable for this type of reaction by reason of thier acid character and their fully determined structure of which the diameters of the intercrystalline channels are of the same order of magnitude as those of the majority of organic molecules.

However, one of the essential drawbacks of these methods for the catalytic processing of methanol on crystalline zeolite is constituted by the rapid deactivation of the catalyst by deposits of carbonaceous origin, which prevents any industrial development under normal economic conditions.

A modified zeolitic catalyst has been sought enabling the production essentially of unsaturated hydrocarbons having for the most part 2 to 5 carbon atoms, and whose catalytic life span is notably increased.

It is known that mordenite is one of the zeolitic silicates richest in silica. The method described in French Pat. No. 1,411,753 enables synthesis of sodium mordenite with small pores of 4 to 5 Å, of which the formula of the elementary unit is $Na_7Al_7Si_{40}O_{94}$, $24H_2O$. The Si/Al (atomic) ratio is close to 6 for the sodium form.

Previously, particularly according to the teaching of French Pat. No. 2,019,913, it was known that mordenites subjected to alternating multiple cycles starting by processing with steam and then refluxing by an acid, have been proposed as catalytic compositions for the conversion of hydrocarbons.

Acid mordenite, obtained by heat treatment, in air at 650° C. in the ammonium form, is very active in the conversion of methanol into hydrocarbons but its life span is very short. After less than 30 minutes of reaction, it has been observed that the conversion ratio of the methanol, initially 100, becomes less than 1%.

SUMMARY AND OBJECTS OF THE INVENTION

Now, it has been observed that the life span of mordenite engaged in a catalytic processing reaction on methanol is very substantially increased when the Si/Al ratio increases. And it has been discovered that use of a zeolite of the synthetic mordenite type whose Si/Al ratio (atomic) is higher than 80 is determining in the production of hydrocarbons from methanol, as regards the distribution of the product obtained and especially as to the stability of the catalyst over time. Catalysts of the de-aluminised mordenite type in which the Si/Al (atomic) ratio is comprised between 100 and 150 are shown to be particularly advantageous in the conversion of methanol into unsaturated hydrocarbons.

The catalyst according to the invention is advantageously applicable to a catalytic process, in the heterogeneous phase, of transforming methanol into ethylenic hydrocarbons, having essentially from 2 to 5 carbon atoms.

According to this method, the methanol is introduced into a carrier gas, which can be indifferently nitrogen, hydrogen, carbon monoxide or carbon dioxide alone or in admixture. The method is applied in continuous exploitation in a reactor with circulation of the gaseous mixture: methanol-gas diluent gas over the catalyst.

The conversion reaction of the methanol is conducted at a pressure between atmospheric pressure and 20 bars, at a temperature between 350° and 550° C.

The concentration of methanol in the entering gaseous mixture is advantageously between 5 and 60% by volume, preferably 30 to 50%; the hourly volumetric flow rate (LSVH) is between 1 and 5 liters of liquid methanol per liter of catalyst and per hour.

After separation of the hydrocarbons formed, the carrier gas is recycled; the unconverted methanol and the dimethylether are also recyclable.

The de-aluminised catalysts used in the conversion of the methanol are obtained by a de-aluminising treatment.

The de-aluminisation of the mordenite can be carried out by two distinct methods which lead to the production of de-aluminsed catalyst (type I) and doubly de-aluminised (type II).

In the description the following notation has been adopted: NaZ denoting the sodium form of the mordenite, NH$_4$Z the ammonium form, HZ the acid form obtained by decomposition of the ammonium form. It is possible to carry out, for example, a prior exchange of the Na$^+$ cation by NH$_4$$^+$ ions by treating the sodium mordenite with an aqueous solution of an ammonium salt, the non de-aluminised acid mordenite being obtained by heat treatment of the ammonium form.

Double de-aluminisation of the mordenite, of the hydrothermic de-aluminisation type, which consists of a series of alternate acid and hydrothermic treatments, leads from the sodium form mordenite to catalysts of type II, and from the ammonium form mordenite to catalysts of type III; the series of treatments commence always with an acid treatment and end with an acid treatment.

The acid treatment in the one case or the other has the following characteristics. Strong inorganic acids are suitable for this type of treatment, such as sulphuric and hydrochloric acid, preferably hydrochloric acid advantageously at a concentration comprising between 2 N and 9 N. The processing temperature is between 60° and 90° C., the operation being carried out with stirring and under reflux, the content of mordenite being in the vicinity of 400 grammes per liter of acid medium. The processing is continued for a period of some hours.

The hydrothermic treatment involves bringing the mordenite to a temperature between 550° and 680° C., preferably between 600° and 650° C., and keeping it there for several hours, under air-steam mixtures, at atmospheric pressure. The concentration of steam (volume) is between 2.5 and 60%, and preferably between 5 and 35%.

The catalysts of type II and III have a content of residual sodium less than 0.1% by weight.

It has been observed that the extraction of aluminium from the mordenite is largely facilitated by the hydrothermic treatment. The development of the Si/Al ratio according to the two de-aluminisation routes has been studied as a function of the number of cycles. A cycle is denoted as an acid treatment followed by a hydrothermic treatment for the catalysts of type II or III; moreover, it has been observed that a final acid treatment is advantageous.

The acid treatment corresponds by way of example to treatment by 6 N HCl at 80° C. for three hours, and a hydrothermic treatment is conducted at 650° C. for 5 hours. Tests have been carried out on 200 g of mordenite for catalysts of type II or III, the ratio Si/Al in the starting NaZ and NH$_4$Z being 5.7. The following results were obtained:

| Number of cycles | Si/Al (type II or III) |
|---|---|
| 2 | 46 |
| 3 | 82 |

It has been observed that the increase in the temperature of the hydrothermic treatment above 700° C. had a deleterious effect on the stability of the catalyst.

By "life span of the catalyst", what is meant is the period during which the activity is substantially constant, in the type of conversion of the methanol into hydrocarbons; this conversion being complete, this time is that at the end of which the appearance of dimethylether and simultaneously unconverted methanol commences in the reaction mixture.

The performances of the doubly de-aluminised catalysts (type II and III) are superior to those of catalysts de-aluminised by the acid chemical route according to the known techniques (type I). The optimum Si/Al ratio is between 100 and 150. No significant modifications have been observed in this interval in the activity and the distribution of the products obtained. Contrary to the catalysts described previously, the life span in this interval is scarcely sensitive to the Si/Al ratio. On the other hand, the catalysts obtained according to this route from NH$_4$Z or HZ (type III) have an activity and a life span superior to those of the catalysts obtained from NaZ (type II), the product distributions being hardly different. In the operating conditions of a pilot reactor, the life span was respectively greater than 15 h (type II) and then 30 h (type III). They are very selective in ethylenic substances C$_2$–C$_5$, which represent more than 75% of the methanol converted. The major product is propene. The distribution of the products is a function for a given catalytic bed of the operating time of the catalysts and of the kinetic factors of the reaction (contact time, methanol pressure, temperature).

It was observed that the increase in partial pressure of methanol increased the proportion of methylated aromatic compounds, principally the hexamethyl benzene at the expense of the benzene, toluene and xylenes.

A rise in temperature by increasing the conversion level has the consequence, on the one hand of the reduction in the methylated aromatic compounds, on the other hand an increase in the light hydrocarbons (ethylene-propene) at the expense of the heavier hydrocarbons (C$_5$.C$_6$). The increase in the total pressure from 1 to 20 bars absolute increases the proportion of unsaturated hydrocarbons in the aliphatic series.

The characteristics of the various types of catalysts useful in the invention figure in the table.

| CHARACTERISTICS OF THE DIFFERENT TYPES OF MORDENITE | | | | | | | | |
|---|---|---|---|---|---|---|---|---|
| | Composition % by weight | | | | Si/Al | Parameters (Å) | | |
| TYPE | SiO$_2$ | Al$_2$O$_3$ | Na$_2$O | ΔP$_{700°}$ C. | (atom) | a | b | c |
| NaZ | 70.5 | 10.4 | 6.3 | 12.8 | 5.7 | 18.137 | 20.423 | 7.505 |
| NH$_4$Z | 74.9 | 10.7 | <0.1 | 14.3 | 5.9 | 18.152 | 20.292 | 7.49 |
| II | 97.1 | 1 | <0.1 | 1.9 | 82.4 | 18.082 | 20.242 | 7.445 |
| III | 94.7 | 0.9 | <0.1 | 4.4 | 89.3 | 18.085 | 20.197 | 7.445 |

The mordenite crystallises in the orthorhombic system (Group Cmcm), ΔP comprises H$_2$O + NH$_3$.

By reason of the deactivation of the catalysts in a limited time, it is possible to apply the method of the invention with periodic regeneration of the catalysts, by combustion in oxygen of the carbon deposited. This operation is carried out by air diluted with an inert gas, such as nitrogen at a temperature between 450° and 600° C. The hourly volumetric speed under the normal conditions of temperature and pressure (VVH) is between 5,000 and 15,000 h$^{-1}$. The content of O$_2$, close to 2% (Volume) at the beginning of the regeneration is then increased gradually taking care not to exceed 600° C. The duration of this operation is some hours, about 3 hours. The thus generated catalyst recovers its activity and its initial life span. The catalysts were tested both in a micro-reactor and in a pilot reactor.

In the micro-reactor, the catalyst was in powder form, the weight used being variable from 100 to 400 mg. The reaction was carried out at atmospheric pressure. The carrier gas was hydrogen; the methanol pressure, adjusted by a system of saturators, condensers, was limited to about 136 millibars. In the pilot reactor, the catalyst was in the form of pastilles, the forming being achieved by incorporation of a clay binder in the proportion of 10% by weight. The volume used varied from 20 to 80 cm3.

DETAILED DESCRIPTION OF PREFERRED EMBODIMENTS

In these examples the percentages relating to the hydrocarbons formed are expressed with respect to the converted methanol.

C$_n$+ denotes the sum of the hydrocarbons (aromatic compounds excepted) with n carbon atoms and more;

ΣC$_4$H$_8$ denotes the sum of the butenes;

(i+1)C$_4$H$_8$ denotes isobutene plus butene-1;

(t+c)C$_4$H$_8$ denotes transbutane plus cis butene-2;

C$_1$–C$_4$ denotes the sum of the hydrocarbons having from 1 to 4 carbon atoms;

S = 1–4 represents the percentage of olefines in the series $C_1$–$C_4$;

$A_r$ denotes the Aromatics and DME dimethylether.

Example 1. (Comparative) Acid mordenite HZ 400 g of sodium mordenite with small pores and in powder form, of the formula $Na_7Al_7$, $Si_{40}O_{94}$, $24H_2O$ were added to 1 liter of an aqueous solution containing 100 g of ammonium nitrate. The mixture was stirred at a temperature of 60° C. for 4 hours. The mordenite was then recovered by filtration then washed with demineralised water to $pH_7$. The zeolite was then subjected to an identical treatment without prior drying. This operation was renewed a third time. The solid was then dried at 100° C. then roasted in air at 650° C. for 3 h. In this way the acid form called HZ was obtained. The $Na^+$ cations were gradually exchanged in the course of these exchanges by $NH_4^+$ ions. The residual sodium content, intially 4.6%, was after these successive treatments respectively 1.1–0.21 and less than 0.1% by weight of the dried products. The ratio Si/Al (atomic) was little different from that of the starting mordenite, namely 5.7.

Application 100 mg of acid mordenite HZ were placed in a micro reactor of glass situated in an oven. The catalyst was pretreated in situ at 500° C. in air at a flow rate of 2 Nl/h for 2 h. The catalytic bed was then traversed by a gaseous mixture of methanol and hydrogen. The conditions of this test and the distribution of the products obtained are shown below. The life span of this catalyst was very short. After less than 30 minutes of reaction the conversion ratio of the methanol into hydrocarbons was less than 1%, for the following operational conditions: atmospheric pressure, temperature of 450° C., flow rate of methanol 100 mg/h (namely pressure of 37.8 millibars of methanol), the flow rate of hydrogen plus methanol gas being 2 Nl/h.

distribution of the manufactured products after 2 minutes of reaction in percent of methanol converted:

TABLE 1-1

| | |
|---|---|
| Unconverted methanol | 0 |
| Dimethylether | 0 |
| $C_1$–$C_4$ | 75 |
| Light aromatic compounds $\leq C_9$ | 5 |
| $C_5^+$ | <1 |
| A | ~20 |

Distribution $C_1$–$C_4$

| | |
|---|---|
| $CH_4$ | 1.6 |
| $C_2H_4$ | 35 |
| $C_2H_6$ | 8.9 |
| $C_3H_6$ | 11.1 |
| $C_3H_8$ | 36.5 |
| iso $C_4H_{10}$ | 3 |
| n $C_4H_{10}$ | 2.8 |
| $\Sigma$ $C_4H_8$ | 1.1 |
| | 100.0 |

Example 2. Doubly de-aluminised mordenite 2.1. from mordenite NaZ

Into a flask of 2.5 l were introduced successively 400 g of sodium mordenite in powder form and 1 l of an aqueous solution of HCl of 6 N normality; the suspension was stirred under reflux for 5 h at a temperature of 90° C. The mordenite was separated by filtration then washed with 10 liters of demineralised water. The pH was then close to 5. This catalyst was then subjected to a hydrothermic treatment, at atmospheric pressure, in a horizontal furnace swept by an air current at the rate of 250 Nl/h. The temperature increased gradually to 650° C. at the rate of 150° C./h. The steam was introduced in to the air from 300° C. Its content was adjusted by means of a saturator. The water flow rate was under our conditions close to 80 g/h namely a content by volume in the air-steam mixture of about 28%. After 5 h at a steady level at 650° C. under these conditions, the supply of the oven was cut off. The cooling was carried out at the speed of the furnace under an air-steam sweep; from 300° C., the steam was stopped. The mordenite was then taken up again with HCl under the same conditions and then subjected to an identical hydrothermic treatment. The operation (acid and hydrothermic treatment) is renewed a 3rd time. The content of $Al_2O_3$ in the product was 1% and the ratio Si/Al (atomic) 82.4. The characteristics of this de-aluminised mordenite of type II, composition % by weight, and cell parameters in Å are indicated below:

| | Composition % by weight | | | | | Parameters (Å) | | |
|---|---|---|---|---|---|---|---|---|
| Type | $SiO_2$ | $Al_2O_3$ | $Na_2O$ | $\Delta P_{700°\ C.}$ | Si/Al (atom) | a | b | c |
| II | 97.1 | 1 | <0.1 | 1.9 | 82.4 | 18.082 | 20.242 | 7.445 |

Application

A—Placing in operation in micro-reactor 100 g of this catalyst in powder form was subjected to catalytic tests for the conversion of methanol in a micro-reactor at atmospheric pressure; the temperature of the reaction was 450° C., and the carrier gas was hydrogen at a flow rate of 2 Nl/h, that of the methanol being 100 mg/h, namely a pressure of $CH_3OH$ of 37.8 millibars. The study of the development of the activity of the catalyst over time follows.

TABLE 2-1

| Duration of operation | $CH_3OH$ unconverted | $C_1$–$C_4$ | Ar | $C_5^+$ | DME | $S_1=4$ |
|---|---|---|---|---|---|---|
| 2' | 2 | 69 | 9 | 20 | <1 | 78 |
| 2 h | 3 | 68 | 8 | 22 | 1 | 86 |
| 5 h | 4 | 67 | 7 | 20 | 2 | 89 |
| 7 h | 6 | 65 | 7 | 19 | 3 | 90 |
| 22 h | 9 | 62 | 6 | 19 | 4 | 95 |

TABLE 2-2

| Duration of operation | Distribution $C_1$-$C_4$. Figures expressed in % $CH_3OH$ converted. | | | | | | | |
|---|---|---|---|---|---|---|---|---|
| | $CH_4$ | $C_2H_4$ | $C_2H_6$ | $C_3H_6$ | $C_3H_8$ | $iC_4H_{10}$ | $(i + 1)$ $C_4H_8$ | $nC_4H_{10}$ | $t + c$ $C_4H_8$ |
| 2' | 1 | 13 | <0.1 | 51 | 11 | 9 | 8 | 0.8 | 6.2 |
| 5 h | 1 | 3.5 | <0.1 | 64 | 3.5 | 5.5 | 13.1 | 0.3 | 8.5 |
| 22 h | 1 | 2 | ~0.1 | 63 | 1 | 2.9 | 16.5 | 0.2 | 13.4 |

Among the aromatics, the principal product is hexamethyl-benzene, representing more than 50% of the aromatics formed. It is formed essentially from methylated derivatives whose content increases with the degree of substitution.

The influence of the conversion temperature of the methanol was studied, in the presence of the doubly de-aluminised catalyst from NaZ, after 26 hours operation at 450° C., under the operating conditions in a micro-reactor.

TABLE 2-3

| | Degree of conversion of the methanol % | | | | | |
|---|---|---|---|---|---|---|
| t° C. | Unconverted $CH_3OH$ | $C_1$-$C_4$ | $S_1$=$^4$ | Ar | DME | $C_5^+$ |
| 400 | 23 | 41 | 96 | 3 | 18 | 15 |
| 450 | 15 | 55 | 95 | 3 | 9 | 18 |
| 500 | 9 | 63 | 93 | 4 | 5 | 19 |

B—Placing in operation in a pilot reactor

In a vertical straight reactor, 40 cm3 of the pastilled catalyst (3×2 mm) containing 10% by weight of a clayey binder was charged. The mass of catalyst was 27 g, namely 24.3 g of mordenite. It was pretreated in situ, at an air flow rate of 250 Nl/h at 500° C. for 2 hours. After this activation period, the reactor was fed continuously from above downwards with a methanol-nitrogen mixture preheated at 400° C. The methanol injected by a pump was, before mixing with the vector $N_2$, vaporised in a preheater.

The kinetic parameters in the reaction were varied: temperature, flow rate, partial pressure of methanol as well as total pressure of the atmospheric pressure at 15 bars absolute.

All of these results are collected in the tables below.

TABLE 2-4

Influence of total flow rate ($N_2$ + $CH_3OH$) at constant methanol pressure.
Average temperature 475° C., pressure of the methanol 109.3 millibars.
Evolution of methanol unconverted into hydrocarbons.

| $N_2$ + $CH_3OH$ flow rate Nl/h | Duration of operation | Unconverted $CH_3OH$ + dimethyl-ether | LSVH $h^{-1}$ | Actual contact time | $VVH_{h-1}$ gas |
|---|---|---|---|---|---|
| 280 | 1 h | 7 | 1.25 | 0.19 s | 7.000 |
| | 3 h | 9 | | | |
| | 6 h | 15 | | | |
| 840 | 1 h | 28 | 3.75 | 0.06 s | 21.000 |
| | 3 h | 29 | | | |
| | 6 h | 38 | | | |

LSVH $h^{-1}$: flow rate of liquid methanol (l) liter catalyst/hour.

TABLE 2-5

Influence of the methanol partial pressure. Evolution of methanol converted into hydrocarbons as a function of time. Constant $CH_3OH$ flow rate 40 g/h, tc = 450° C. (means), vector $N_2$.

| Flow rate $N_2$N l/h | p.$CH_3OH$ mb | $VVH_{h-1}$ gas | Actual contact time | t operation | $CH_3OH$ %* converted |
|---|---|---|---|---|---|
| 500 | 57.3 | 13,250 | 0.11 | 1 h | 72 |
| | | | | 6 h | 66 |
| | | | | 24 h | 58 |
| 250 | 108 | 7,000 | 0.22 | 2 h | 90 |
| | | | | 5 h | 83 |
| | | | | 13 h | 67 |
| 150 | 169 | 4,500 | 0.36 | 1 h | 98 |
| | | | | 5 h | 68 |
| | | | | 10 h | 40 |

*this figure corresponds to the degree of conversion of the $CH_3OH$ into hydrocarbons, it does not comprise the dimethylether.
2-b A from mordenite $NH_4Z$.

200 g of sodium mordenite with small pores were subjected to an identical treatment with that described in Example 1; by this method the ammonium form $NH_4Z$ was obtained. The product was dried in the oven at 100° C. then de-aluminised according to the procedure described in the preceding example (3 successive cycles of alternate acid and hydrothermic treatments).

The product obtained had a content of $Al_2O_3$ of 0.9% and an Si/Al ratio of about 90. This composition and the mesh parameters were as follows:

| | Compositions % Weight | | | | | Parameters (Å) | | |
|---|---|---|---|---|---|---|---|---|
| Type | $SiO_2$ | $Al_2O_3$ | $Na_2O$ | $\Delta P_{700°\ C.}$ | Si/Al (atom) | a | b | c |
| III | 94.7 | 0.9 | <0.1 | 4.4 | 89.3 | 18.085 | 20.197 | 7.445 |

This catalyst was subjected to tests in a micro-reactor and pilot reactor under the previously described conditions. The whole of the results indicated below relate to the pilot reactor.

This catalyst has, with respect to the one de-aluminised from NaZ, superior performance as to activity and life span.

The kinetic parameters of the reaction were also varied: temperature, partial pressure of methanol flow rate. The results are on the whole in agreement with those obtained with the preceding catalyst. The distribution of the product is similar; on the other hand the de-activation speed is much less sensitive to the increase in the partial pressure of methanol with this catalyst than with the preceding one. Thus, with a methanol flow rate of 40 g/h, the life span of the catalyst ($CH_3OH$ conversion into hydrocarbons >90%) was greater than 40 hours with an $N_2$ flow rate of 250 Nl/h, namely methanol pressure of 108 millibars; it was again 35 hours when the nitrogen flow rate was lowered to 50 Nl/h, namely a methanol pressure of 380 millibars.

The selectivity developed with a function of time. In particular the ethylene and isobutane production diminishes at the expense of the propene and the isobutene. The cut $C_1$–$C_4$ represents more than 70% of the converted methanol, the selectivity in unsaturated products being greater than 90%. The predominant product was propene. In the series of the aromatics it was essentially methylated derivatives whose content increased with the degree of substitution; the predominant product was hexamethylbenzene.

The total pressure was also varied from atmospheric pressure to 20 bars absolute. The life span of the catalyst was not improved. On the other hand, the distribution of the products manufactured was modified in favor of the unsaturates.

Comparison of the "doubly de-aluminised" mordenites from NaZ (type II) and NH$_4$Z (type III). Operating conditions: Pilot reactor volume 40 cm3, catalyst in pastilles 3×3 mm, temperature 450° C., atmospheric pressure, flow rate of nitrogen carrier gas N$_2$250 Nl/h, flow rate CH$_3$OH 40 g/h. Development of the degree of conversion of the methanol into hydrocarbons, the dimethylether not being accounted in the figures indicated.

TABLE 2-6

| Operating time; catalyst type III | | Operating time; catalyst, type II | |
|---|---|---|---|
| 2 h | 98.2 | 1 h | 93 |
| 18 h | 97.5 | 3 h | 91 |
| 27 h | 96.2 | 6 h | 90 |
| 34 h | 93.5 | 12 h | 86 |
| 42 h | 91.2 | 20 h | 77 |

Under the same operating conditions applied with the doubly de-aluminised catalyst of type III, the average distribution of the products manufactured over 35 hours of reaction, were studied.

TABLE 2-7

| Degree of conversion of methanol % | |
|---|---|
| Unconverted CH$_3$OH | 2.3 |
| Dimethylether | 1.2 |
| C$_1$ | 1.3 |
| C$_2$H$_4$ | 5.9 |
| C$_2$H$_6$ | <0.1 |
| C$_3$H$_6$ | 49.5 |
| C$_3$H$_8$ | 0.7 |
| C$_4$ S | 2.9 |
| C$_4$ S= | 14.5 |
| C$_5$ S | 1 |
| C$_5$ S= | 9 |
| C$_6$+ | 6 |
| Aromatics | 5.2 |
| CoKe + CO + CO$_2$ | ~0.5 |
| | 100.0 |

TABLE 2-8

| Distribution % C$_4$ | |
|---|---|
| Isobutane | 12.1 |
| n-butane | 1 |
| butene-1 | 7.1 |
| Isobutene | 39 |
| Trans 2-butene | 23.3 |
| cis 2-butene | 17.5 |

TABLE 2-8-continued

| Distribution % C$_4$ | |
|---|---|
| | 100.00 |

TABLE 2-9

| Distribution % C$_5$ | |
|---|---|
| Methyl-3 butene-1 | 3.4 |
| Isopentane | 7.5 |
| pentene-1 | 5.4 |
| methyl-2 butene-1 | 18.5 |
| n-pentane | 4 |
| trans-2 pentene | 16.2 |
| cis-2 pentene | 8.4 |
| methyl-2 butene-2 | 35.6 |
| cyclopentane + cyclopentene | 1 |
| | 100.0 |

In addition, the influence of the total pressure on the distribution of the products $C_1$–$C_5$ (% CH$_3$OH converted) was studied after 2 hours of reaction conducted in a pilot reactor with a catalyst volume of 40 cm3 in pastilles 3×3 mm, the flow rates of N$_2$ being 750 Nl/h and CH$_3$OH 120 g/h.

TABLE 2-10

| Pressure | CH$_4$ | C$_2$H$_4$ | C$_2$H$_6$ | C$_3$H$_6$ | C$_3$H$_8$ | iC$_4$H$_{10}$ | (i + 1) C$_4$H$_8$ | nC$_4$H$_{10}$ | butene-2 | C$_5$S | C$_5$S= |
|---|---|---|---|---|---|---|---|---|---|---|---|
| Atm. | 0.6 | 3.8 | 0.1 | 31 | 0.8 | 1.1 | 7.1 | 0.1 | 3.5 | 1 | 7.2 |
| 10 bars | 1.3 | 3.9 | 0.1 | 25 | 2.2 | 5.2 | 5.5 | 0.8 | 3.2 | 2.8 | 4.4 |

The production of hydrocarbons per kilogramme of catalyst in 35 hours of operation, 57.6 kg of methanol having passed through the catalyst would be as follows:

| | Kg | in >—CH$_2$ |
|---|---|---|
| Unconverted methanol | 1.33 | 0.52. |
| dimethyl ether | 0.69 | 0.30 |
| CH$_4$ | 0.75 | 0.33 |
| C$_2$H$_4$ | 3.4 | 1.48 |
| C$_3$H$_6$ | 28.51 | 12.46 |
| C$_3$H$_8$ | 0.40 | 0.18 |
| C$_4$S | 1.67 | 0.73 |
| C$_4$S= | 8.35 | 3.65 |
| C$_5$S | 0.58 | 0.25 |
| C$_5$S= | 5.18 | 2.27 |
| C$_6$+ | 3.46 | 1.51 |
| Aromatics | 3 | 1.31 |
| Coke + CO + CO$_2$ | 0.12 | 0.12 |
| | 57.6 | 27.17 kg hydrocarbons |

Example 3

600 g of sodium mordenite were converted into the ammonium form according to the procedure described in Example 1. The temperature of each treatment was 80° C. The content of Na was less than 0.05% by weight. This product was subjected to a double de-aluminisation, such as described in Example 2a, applying successively hydrochloric and hydrothermic treatments. The temperature of the acid treatment was 90° C. and that of the hydrothermic treatment 650° C.; the steam content (% Vol) of the air-steam mixture was 15%. The content of Al$_2$O$_3$ of the dried product was after 2 cycles 0.9%. This de-aluminised mordenite was subjected to a complementary hydrochloric treatment under conditions identical with the preceding one (HCl 6 N-90° C.). The Al$_2$O$_3$ content was then 0.7% (Si-/Al>100)=120. This catalyst was subjected to tests in a pilot reactor according to the operation described in examples 2a and b.

The operating conditions were as follows:
CH$_3$OH: 40 g/h
Carrier N$_2$: 50 Nl/h
Atmospheric pressure
Average temperature: 470° C.

The conversion of the methanol into hydrocarbons was complete. The distribution of the product obtained was in the vicinity of that shown in Table 2-7 with however a slight reduction in the ethylene content. The life span of the catalyst was increased with respect to the catalyst of Example 2b where de-aluminisation was terminated by hydrothermic treatment. After 50 h of operation the degree of the conversion of the methanol into hydrocarbons was greater than 90%.

Degree of conversion of the methanol:

| | |
|---|---|
| CH$_4$ | 1.2 |
| C$_2$H$_4$ | 3.2 |
| C$_2$H$_6$ | 0.1 |
| C$_3$H$_6$ | 53 |
| C$_3$H$_8$ | 1.1 |
| C$_4$H$_8$ | 16.8 |
| C$_4$H$_{10}$ | 4.3 |
| C$_5$H$_{10}$ | 7.8 |
| C$_5$H$_{12}$ | 1.2 |
| C$_6$$^+$ | 6 |
| Aromatics | 5 |
| "coke" + CO + CO$_2$ | 0.3 |

Example 4

200 g of de-aluminised mordenite were prepared according to the procedure described in Example 2b:

Preparation of NH$_4$Z from NaZ followed by de-alumination by alternate HCl and hydrothermic treatments. The conditions of the acid treatment were identical; on the other hand, the content of steam in the air-steam mixture was lowered to 2.5% (Vol), the other parameters (temperature, time, flow rate) being unchanged. The product obtained after 3 cycles had a content in Al$_2$O$_3$ of 1.2%. This catalyst was tested in a pilot reactor under identical conditions after shaping (pastilles of 3 mm diameter, 10% binder). The operating conditions were the following: CH$_3$OH: 40 g/h; N$_2$: 50 Nl/h; Atmospheric pressure; average temperature: 470° C.

The life span of this catalyst was between 10 and 15 h. After 20 h of reaction, the conversion ratio of the methanol into hydrocarbons was less than 50%. (The complement to 100 being dimethylether and unconverted methanol).

The distribution of the products was substantially different from the preceding example (2b), particularly at the level of the cut C$_4$ and C$_5$ where there was noted an increase in saturates. The predominant product of the cut C$_4$ was isobutane. It decreases in the course of time to the advantage of the isobutene but much less than in the other cases. There is indicated below, the comparative development of the ratio iso C$_4$H$_{10}$/iso C$_4$H$_8$.

| Reaction time | Example | Example 3b |
|---|---|---|
| 1 h | 3.8 | 0.9 |
| 4 h | 2.2 | 0.45 |
| 10 h | 1.1 | 0.2 |

The distribution of the products obtained (by carbon atoms) is on the other hand very little modified. Propene remains the predominant product (>50%/methanol converted).

We claim:

1. Method of producing light olefinic hydrocarbons having 2-5 carbons from methanol, in particular unsaturated hydrocarbons, in the presence of a zeolitic mordenite catalyst, wherein gasified methanol introduced into a carrier gas, the concentration of the methanol in an entering mixture being between 5 and 60% by volume, is passed through a catalytic bed based on dealuminised synthetic mordenite whose Si/Al ratio (atomic) is higher than 80, the methanol flow rate being between 1 and 5 liters of liquid methanol per liter of catalyst and per hour, the reaction being carried out at a temperature between 350° and 550° C., under a pressure which can reach 20 bars;

said synthetic mordenite having been de-aluminised by subjecting the mordenite to a series of alternate acid and hydrothermic treatments; during the acid treatment phase, subjecting the mordenite to treatment in a concentrated acid medium, at a temperature between 60° and 90° C., with stirring for some hours; in the hydrothermic treatment phase, bringing the mordenite to a temperature between 550° and 680° C. for some hours, at atmospheric pressure, in an air-steam mixture of which the air-steam flow rate under normal conditions of temperature and pressure is between 500 and 1250 l/h for a weight of catalyst of 1 kg, the steam concentration by volume being between 2.5 and 60%; the series of treatments commencing with an acid treatment and terminating with an acid treatment.

2. Method of producing hydrocarbons from methanol, according to claim 1, wherein said Si/Al ratio is between 100 and 150.

3. Method of producing hydrocarbons from methanol, according to claim 1 or 2, wherein the concentration of the entering methanol is between 30 and 50% by volume.

4. Method of producing hydrocarbons from methanol, according to claim 1 or 2, wherein unconverted methanol is recycled, possibly conjointly with the dimethylether formed, also recycled.

5. Method of producing hydrocarbons from methanol according to claim 3, wherein unconverted methanol is recycled, if necessary conjointly with a dimethylether formed, also recycled.

6. Method of producing hydrocarbons from methanol according to claim 1 or 2, wherein the method is applied with periodic regeneration of the catalyst by combustion in oxygen diluted with an inert gas, at a temperature between 450° and 600° C. for some hours, the hourly volumetric speed under normal conditions of temperature and pressure being between 5,000 and 15,000 h$^{-1}$, the oxygen content being of the order of 2% by volume at the start of the regeneration, with gradual increase without exceeding the temperature of 600° C.

7. Process of producing hydrocarbons from methanol according to claim 3, wherein the method is applied with periodic regeneration of the catalyst by combustion in oxygen diluted with an inert gas, at a temperature between 450° and 600° C. for some hours, the hourly volumetric speed under normal conditions of temperature and pressure being between 5,000 and 15,000 $h^{-1}$, the oxygen content being of the order of 2% by volume at the start of the regeneration, with gradual increase without exceeding the temperature of 600° C.

8. Method of producing hydrocarbons from methanol according to claim 3, wherein unconverted methanol is recycled, if necessary conjointly with dimethylether formed, also recycled, and the method is applied with periodic regeneration of the catalyst by combustion in oxygen diluted with an inert gas, at a temperature between 450° and 600° C. for some hours, the hourly volumetric speed under normal conditions of temperature and pressure being between 5,000 and 15,000 $h^{-1}$, the oxygen content being of the order of 2% by volume at the start of the regeneration, with gradual increase without exceeding the temperature of 600° C.

9. Method for the hydrothermic de-aluminisation of mordenite, comprising subjecting the mordenite to a series of alternate acid and hydrothermic treatments; during the acid treatment phase, subjecting the mordenite to treatment in a concentrated acid medium, at a temperature between 60° and 90° C., with stirring for some hours; in the hydrothermic treatment phase, bringing the mordenite to a temperature between 550° and 680° C. for some hours, at atmospheric pressure, in an air-steam mixture of which the air-steam flow rate under normal conditions of temperature and pressure is between 500 and 1250 l/h for a weight of catalyst of 1 kg, the steam concentration by volume being between 2.5 and 60%; the series of treatments commencing with an acid treatment and terminating by an acid treatment.

10. Method of hydrothermic de-aluminisation of mordenite, according to claim 9, wherein the concentrated acid medium has a normality between 2 and 9 N.

11. Method of hydrothermic de-aluminisation fof mordenite, according to claim 9, wherein in the hydrothermic treatment phase the mordenite is brought to a temperature between 600° and 650° C.

12. Method of hydrothermic de-aluminisation of mordenite, according to claim 9, wherein the concentration of steam by volume in the air-steam mixture is between 5 and 35%.

13. Method of hydrothermic de-aluminisation of mordenite, according to claim 10, wherein during the hydrothermic treatment phase the mordenite is brought to a temperature between 600° and 650° C., and wherein the air-steam mixture has a steam concentration by volume between 5 and 35%.

14. Doubly de-aluminised mordenite obtained by the method according to claim 9, 10, 11, 12, or 13 wherein the starting material is sodium mordenite.

15. Doubly de-aluminised mordenite obtained by the method according to claim 9, 10, 11, 12, or 13, wherein the starting material is ammonium form mordenite.

* * * * *